(12) United States Patent
Yoshino

(10) Patent No.: US 9,888,831 B2
(45) Date of Patent: Feb. 13, 2018

(54) IMAGING DEVICE AND IMAGING METHOD

(71) Applicant: OLYMPUS CORPORATION, Shibuya-ku, Tokyo (JP)

(72) Inventor: Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 662 days.

(21) Appl. No.: 14/049,046

(22) Filed: Oct. 8, 2013

(65) Prior Publication Data
US 2014/0036050 A1 Feb. 6, 2014

Related U.S. Application Data

(63) Continuation of application No. PCT/JP2012/059493, filed on Apr. 6, 2012.

(30) Foreign Application Priority Data

Apr. 11, 2011 (JP) ................................. 2011-087477

(51) Int. Cl.
*H04N 9/47* (2006.01)
*H04N 7/18* (2006.01)
(Continued)

(52) U.S. Cl.
CPC ........ *A61B 1/00009* (2013.01); *G06T 3/0012* (2013.01); *G06T 3/0018* (2013.01);
(Continued)

(58) Field of Classification Search
CPC .......... A61B 1/00; A61B 1/00009; G06T 1/00
(Continued)

(56) References Cited

U.S. PATENT DOCUMENTS

| 5,818,527 | A | 10/1998 | Yamaguchi et al. |
| 7,918,614 | B2 | 4/2011 | Wernersson |
| 2005/0201641 | A1* | 9/2005 | Owen ............... G06T 3/0012 |
| | | | 382/298 |
| 2007/0172230 | A1 | 7/2007 | Wernersson |
| 2009/0202177 | A1 | 8/2009 | Jeffrey |

(Continued)

FOREIGN PATENT DOCUMENTS

| JP | 08-256295 A | 10/1996 |
| JP | 2005-345577 A | 12/2005 |

(Continued)

OTHER PUBLICATIONS

International Search Report (ISR) dated May 15, 2012 (and English translation thereof) in International Application No. PCT/JP2012/059493.

(Continued)

*Primary Examiner* — Mehrdad Dastouri
*Assistant Examiner* — Kristin Dobbs
(74) *Attorney, Agent, or Firm* — Holtz, Holtz & Volek PC

(57) ABSTRACT

The imaging device includes an image sensor that includes a plurality of pixels that generate an image signal from an object image that is formed by an imaging optical system, a scaling section that performs a scaling process on an original image that includes image signals that correspond to the plurality of pixels, and an output section that outputs an image after the scaling process as a scaled image, the scaling section performing the scaling process using a different scaling factor corresponding to the position of a pixel of interest within the scaled image, and the image sensor including pixels in a number larger than the number of pixels of the scaled image as the plurality of pixels.

18 Claims, 12 Drawing Sheets

(51) Int. Cl.

| | |
|---|---|
| *A62B 1/04* | (2006.01) |
| *A61B 1/00* | (2006.01) |
| *H04N 5/357* | (2011.01) |
| *H04N 5/232* | (2006.01) |
| *G06T 3/00* | (2006.01) |
| *G03B 37/00* | (2006.01) |
| *H04N 5/225* | (2006.01) |

(52) U.S. Cl.
CPC ..... *H04N 5/23229* (2013.01); *H04N 5/23296* (2013.01); *H04N 5/3572* (2013.01); *A61B 1/00188* (2013.01); *G03B 37/005* (2013.01); *H04N 2005/2255* (2013.01)

(58) Field of Classification Search
USPC .......................................................... 348/65
See application file for complete search history.

(56) References Cited

U.S. PATENT DOCUMENTS

2009/0278920 A1* 11/2009 Kamo .................. G02B 23/243
    348/65

FOREIGN PATENT DOCUMENTS

| | | |
|---|---|---|
| JP | 2007-306199 A | 11/2007 |
| JP | 2009-276371 A | 11/2009 |
| SE | WO 2007082591 A1 * | 7/2007 ........... H04N 5/2251 |
| WO | 2007082591 A1 | 7/2007 |

OTHER PUBLICATIONS

Extended European Search Report dated Aug. 5, 2014 in counterpart European Application No. 12771335.2.

* cited by examiner

FIG. 16

| | K | P[mm] | Fno. | f[mm] | IN-FOCUS OBJECT PLANE [nm] | NEAR POINT [nm] | FAR POINT [nm] |
|---|---|---|---|---|---|---|---|
| NORMAL | 3 | 0.004 | 12 | 1.8 | −16.0 | −8.9 | −79.9 |
| SUPER-WIDE ANGLE | 3 | 0.002 | 12 | 1.2 | −15.0 | −6.0 | −113.4 |

IMAGING DEVICE AND IMAGING METHOD

CROSS REFERENCE TO RELATED APPLICATION

This application is a continuation of International Patent Application No. PCT/JP2012/059493, having an international filing date of Apr. 6, 2012, which designated the United States, the entirety of which is incorporated herein by reference. Japanese Patent Application No. 2011-087477 filed on Apr. 11, 2011 is also incorporated herein by reference in its entirety.

BACKGROUND

The present invention relates to an imaging device, an imaging method, and the like.

It is desirable that an imaging device such as an endoscope system utilize a wide-angle optical system in order to suppress a situation in which a lesion area situated on the back side of folds is missed when observing a large intestine, for example. The angle of view of the optical system used for an endoscope system is normally about 140 to 170°. It is possible to further suppress a situation in which a lesion area is missed by utilizing a super-wide-angle optical system having an angle of view equal to or greater than 180° (see JP-A-2005-345577, for example).

SUMMARY

According to one aspect of the invention, there is provided an imaging device comprising:

an image sensor that includes a plurality of pixels that generate image signals from an object image that is formed by an imaging optical system;

a scaling section that performs a scaling process on an original image that is based on the image signals generated by the plurality of pixels; and an output section that outputs an image obtained by the scaling process as a scaled image, the scaling section performing the scaling process using a different scaling factor corresponding to a position of a pixel of interest within the scaled image, and the image sensor including pixels in a number larger than a number of pixels of the scaled image as the plurality of pixels.

According to another aspect of the invention, there is provided an imaging method comprising:

acquiring an original image based on image signals generated by a plurality of pixels that generate image signals from an object image that is formed by an imaging optical system;

performing a scaling process on the original image using a different scaling factor corresponding to a position of a pixel of interest to acquire a scaled image, the scaled image being an image having a number of pixels smaller than that of the original image; and outputting an image obtained by the scaling process as the scaled image.

BRIEF DESCRIPTION OF THE DRAWINGS

FIG. 16 is a view illustrating the characteristics of a normal optical system and a wide-angle optical system according to one embodiment of the invention.

DESCRIPTION OF EXEMPLARY EMBODIMENTS

Figure 1:
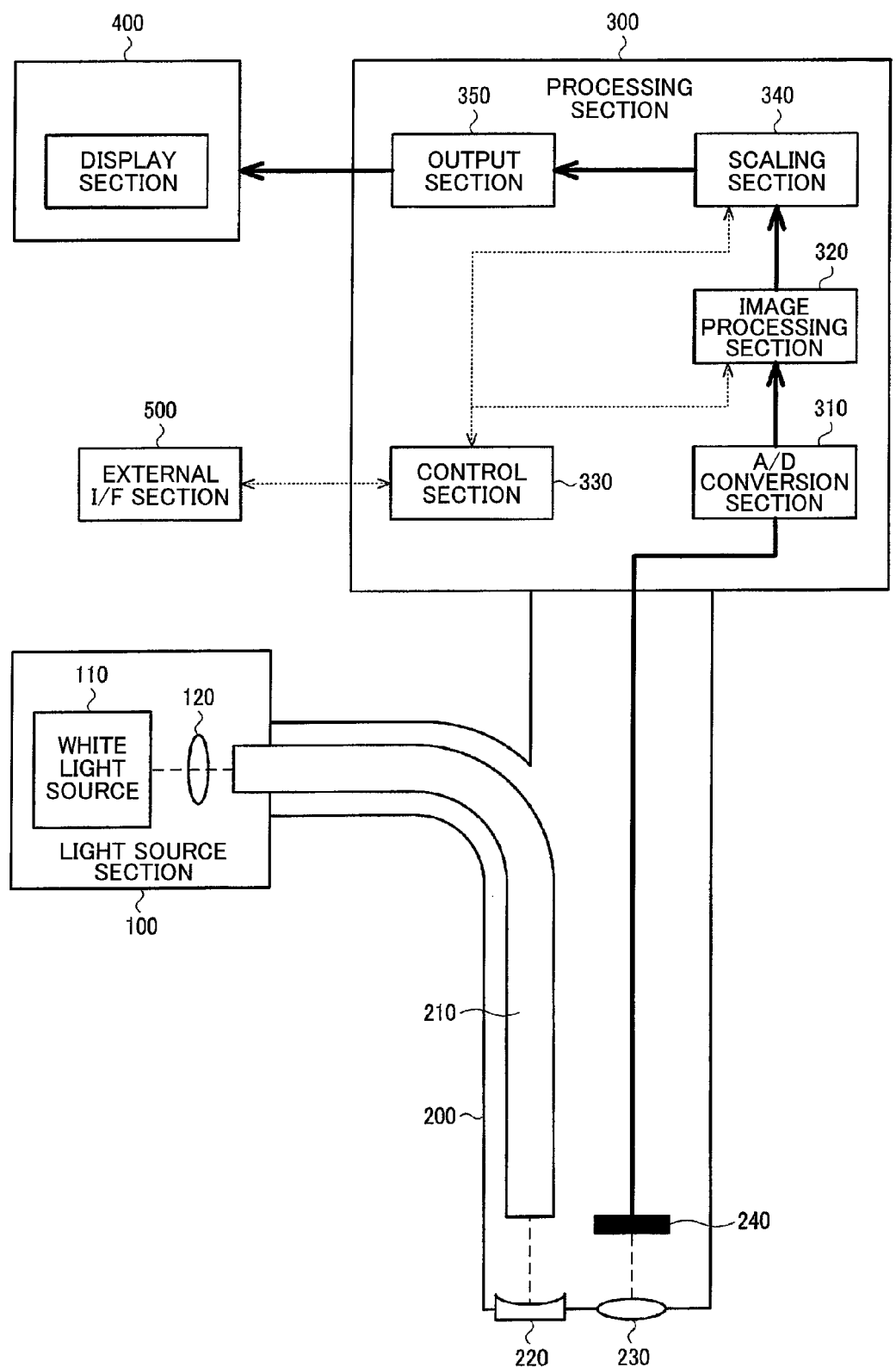
FIG. 1 illustrates a system configuration example according to one embodiment of the invention.

According to one embodiment of the invention, there is provided an imaging device comprising:

an image sensor that includes a plurality of pixels that generate image signals from an object image that is formed by an imaging optical system;

a scaling section that performs a scaling process on an original image that is based on the image signals generated by the plurality of pixels; and an output section that outputs an image obtained by the scaling process as a scaled image, the scaling section performing the scaling process using a different scaling factor corresponding to a position of a pixel of interest within the scaled image, and the image sensor including pixels in a number larger than a number of pixels of the scaled image as the plurality of pixels.

According to another embodiment of the invention, there is provided an imaging method comprising:

acquiring an original image based on image signals generated by a plurality of pixels that generate image signals from an object image that is formed by an imaging optical system;

performing a scaling process on the original image using a different scaling factor corresponding to a position of a pixel of interest to acquire a scaled image, the scaled image being an image having a number of pixels smaller than that of the original image; and outputting an image obtained by the scaling process as the scaled image.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method employed in several embodiments of the invention is described below. An imaging device such as an endoscope apparatus may be implemented using an optical system having an angle of view (e.g., 180° or more) wider than that (e.g., 140 to 170°) of a normal imaging optical system. Specifically, when the back side of folds is sufficiently observed within the imaging range when observing a large intestine or the like, it is possible to capture a lesion area or the like that is present in an area that is difficult to observe using a normal optical system.

When using a wide-angle optical system, an image is distorted due to the effects of distortion or the like. For example, the peripheral area of the image may become unclear as compared with the center area of the image. This problem may be solved by canceling the distortion of the image by enlarging an area (e.g., peripheral area) in which the local magnification is low to acquire an image that can be easily observed, for example.

However, since an unclear area is enlarged by such a method, the lesion is enlarged, but the resolution of the image decreases in the enlargement target area, and blurring (defocusing) or the like may occur.

In order to deal with the above problem, several embodiments of the invention employ the following method. Specifically, an image sensor captures an image (original image) having a resolution higher that of (i.e., having a number of pixels larger than that of) an image (scaled image) displayed on a display section. A scaling process is performed on an unclear area in which the local magnification is low using a scaling factor of about 1. In contrast, a reduction process is performed on a clear area in which the local magnification is high using a scaling factor of $\beta$. When the ratio of the length of one side of the original image to the length of one side of the scaled image is referred to as $\alpha$ ($\alpha>1$), $\beta$ is smaller than ($1/\alpha$). Specifically, the scaled image and the original image have an equal degree of distortion when the reduction process is equally performed on the entire original image using a scaling factor of $1/\alpha$. According to the method employed in several embodiments of the invention, distortion is canceled by decreasing the reduction factor (preferably setting the reduction factor to 1) in the peripheral area, and increasing the reduction factor to be larger than $1/\alpha$ in the center area. The method employed in several embodiments of the invention is similar to the above method in that the peripheral area is enlarged relative to the center area. However, since the method employed in several embodiments of the invention utilizes a high-resolution image as the original image, the scaling factor in the peripheral area can be set to a value close to 1, and a decrease in resolution in the peripheral area can be suppressed. Note that the scaling factor in the peripheral area is not limited to 1.

A system configuration example, the relationship between the angle of view and the depth of field, and the scaling process are described in detail below.

2. System Configuration Example

An endoscope system (i.e., imaging device) according to one embodiment of the invention is described below with reference to FIG. 1. The endoscope system according to one embodiment of the invention includes a light source section 100, an imaging section 200, a processing section 300, a display section 400, and an external I/F section 500.

The light source section 100 includes a white light source 110 that emits white light, and a condenser lens 120 that focuses the emitted white light on a light guide fiber 210.

The imaging section 200 is formed to be elongated and flexible so that the imaging section 200 can be inserted into a body cavity or the like. The imaging section 200 includes the light guide fiber 210 that guides the light focused by the light source section 100, an illumination lens 220 that diffuses the light that has been guided by the light guide fiber 210, and applies the diffused light to the observation target, an objective lens 230 that focuses light reflected by the observation target, and an image sensor 240 that detects the focused reflected light. The objective lens 230 is a super-wide-angle lens having an angle of view of about 220°, for example. The image sensor 240 includes a Bayer color filter array, for example.

The processing section 300 includes an A/D conversion section 310, an image processing section 320, a control section 330, a scaling section 340, and an output section 350. Note that the processing section 300 is not limited to the configuration illustrated in FIG. 1. Various modifications may be made, such as omitting some of the elements illustrated in FIG. 1 or adding other elements. The A/D conversion section 310 converts an analog signal output from the image sensor 240 into a digital image signal (hereinafter referred to as "image"), and outputs the digital image to the image processing section 320. The image processing section 320 performs image processing (e.g., white balance process, demosaicing process, color conversion process, and grayscale transformation process) on the image output from the AD conversion section 310, and outputs the resulting image to the scaling section 340. The scaling section 340 performs a scaling process on the image output from the image processing section 320, and outputs the resulting image to the output section 350. The details of the scaling section 340 are described later. The output section 350 converts the image output from the scaling section 340 into an image in a format (digital signal or analog signal) that is supported by the display section 400, and outputs the resulting image to the display section 400. The display section 400 is a liquid crystal monitor, for example. The display section 400 displays the image output from the output section 350.

The control section 330 is bidirectionally connected to the image processing section 320, the scaling section 340, and the external I/F section 500, and controls the image processing section 320, the scaling section 340, and the external I/F section 500 according to input information input from the external I/F section 500. The external I/F section 500 is an interface that allows the user to perform an input operation or the like on the endoscope system (imaging device). The external I/F section 500 includes a start button (imaging start/stop button), an adjustment button for adjusting the imaging conditions and the display conditions, and the like.

3. Relationship Between Angle of View and Depth of Field

The relationship between the angle of view of the objective lens (hereinafter may be referred to as "optical system") and the depth of field of the endoscope system is described below.

A deep depth of field is required for an endoscope system in order to facilitate a doctor's diagnosis. The depth of field of an endoscope system is normally increased by utilizing an optical system having a relatively large F-number. In recent years, an image sensor having about several hundred thousand pixels has been used for an endoscope system. The depth of field of an optical system is determined by the size of the permissible circle of confusion when the optical system is constant. Since an image sensor having a large number of pixels has a small pixel pitch and a small permissible circle of confusion, the depth of field of the imaging device decreases. Moreover, when the F-number of the optical system is increased in order to increase the depth of field, the imaging performance of the optical system deteriorates due to the effects of diffraction. Accordingly, the maximum number of pixels of the image sensor may be limited in order to maintain a depth of field that facilitates a doctor's diagnosis.

The depth of field varies to a large extent depending on the focal length of the optical system in addition to the number of pixels of the image sensor and the F-number of the optical system. The depth of field increases as the focal length decreases. It has been empirically known that the focal length of a super-wide-angle optical system is about ⅔rd of that of an optical system having an angle of view of about 140 to 170° when the size of the image sensor is identical. Therefore, an endoscope system that includes a super-wide-angle optical system allows a reduction in pixel pitch (i.e., an increase in number of pixels of the image sensor) as compared with a normal endoscope system while maintaining a depth of field that facilitates a doctor's diagnosis.

Figure 2:
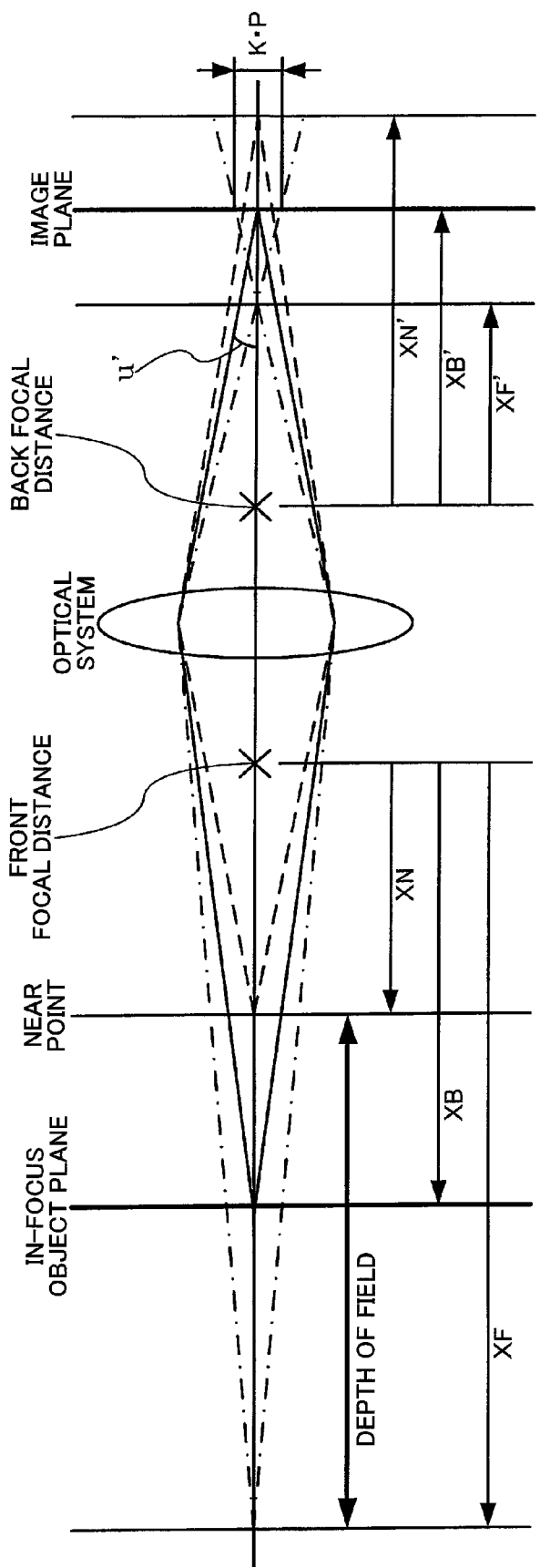
FIG. 2 is a view illustrating the depth of field.

The depth of field is described in detail below with reference to FIG. 2. In FIG. 2, each arrow that points to the right indicates a vector having a positive value, and each arrow that points to the left indicates a vector having a negative value. When an image sensor having a pixel pitch (vertical and horizontal dimensions of one pixel) of P is disposed at a distance XB' from the back focal distance of the optical system, the position (in-focus object plane) of the object at which the optical system has the best imaging performance in the image plane of the image sensor is the position at a distance XB from the front focal distance of the optical system. The distance XB is uniquely calculated by the following Newton's equation using the distance XB'. Note that f is the focal length of the optical system.

$$XB \cdot XB' = -f^2 \quad (1)$$

When the object is moved to the position at a distance XN from the front focal point position of the optical system, the image plane position (XN') moves from the image plane in the direction opposite to the optical system. However, when the diameter of the circle of confusion in the image plane is smaller than the resolution K·P (where, K is a coefficient determined by a filter array and an interpolation process) of the imaging device, the object positioned at the distance XN from the front focal distance of the optical system is considered to be in focus. A range in which the diameter of the circle of confusion in the image plane is equal to or smaller than the resolution K·P is defined as the near point-side depth of field, and the position of the object at which the diameter of the circle of confusion coincides with the resolution K·P is hereinafter referred to as "near point". The near point is the position at the distance XN from the front focal distance. The above definition is similarly applied to the far point-side depth of field. The far point-side position of the object at which the diameter of the circle of confusion coincides with the resolution K·P is hereinafter referred to as "far point". The far point is the position at the distance XF from the front focal distance.

The diameter of the circle of confusion in the image plane when the object is positioned at the near point is approximated by the following expression (2) using the numerical aperture NA" (=sin u') (where, u' is the angle formed by the optical axis and a beam that is incident on the image plane (see FIG. 2)) of the optical system.

$$\text{Diameter of circle of confusion} = 2(XN'-XB') \times NA' \quad (2)$$

Since the diameter of the circle of confusion coincides with the resolution K·P when the object is positioned at the near point, the following expression (3) is satisfied.

$$2(XN'-XB') \cdot NA' = K \cdot P \quad (3)$$

Transforming the expression (3) using the following expression (4) (i.e., the relational expression of the F-number and the numerical aperture) yields the following expression (5). Note that F is the F-number of the optical system.

$$F = \frac{1}{2NA'} \quad (4)$$

$$XN' - XB' = K \cdot P \cdot F \quad (5)$$

Transforming the expression (5) using Newton's equation (1) yields the following expression (6) (i.e., the relational expression of the near point-side depth of field).

$$\frac{1}{XB} - \frac{1}{XN} = \frac{K \cdot P \cdot F}{f^2} \quad (6)$$

The relational expression of the far point-side depth of field calculated in the same manner as the near point-side depth of field is shown by the following expression (7).

$$\frac{1}{XF} - \frac{1}{XB} = \frac{K \cdot P \cdot F}{f^2} \quad (7)$$

The expressions (6) and (7) can be transformed into the following expressions (8) and (9). The position (XN) of the near point and the position (XF) of the far point can be calculated using the expressions (8) and (9). The range between the near point and the far point is hereinafter referred to as "depth of field".

$$XN = \frac{f^2 \cdot XB}{f^2 - KPF \cdot XB} \quad (8)$$

$$XF = \frac{f^2 \cdot XB}{f^2 + KPF \cdot XB} \quad (9)$$

FIG. 16 illustrates an example of the depth of field calculated using the expressions (8) and (9). The depth of field was calculated on the assumption that the focal length of the optical system of a normal endoscope system is 1.8 mm, and the focal length of the optical system of a super-wide angle endoscope system is 1.2 mm (corresponding to ⅔rd of the focal length of the optical system of the normal endoscope system). The related values are also illustrated in FIG. 16. As illustrated in FIG. 16, the super-wide angle endoscope system can achieve a deeper depth of field even though the pixel pitch of the super-wide angle endoscope system is half of that of the normal endoscope system. Note that it is necessary to decrease the F-number when reducing the pixel pitch so that the optical system achieves sufficient imaging performance since the effects of diffraction increase. However, qualitative results are obtained that indicate that the super-wide-angle endoscope system allows a reduction in pixel pitch (i.e., an increase in number of pixels of the image sensor) as compared with the normal endoscope system even if such an adjustment is made.

4. Scaling Process

The details of the scaling section 340 are described below. The following description is given on the assumption that the number of pixels of the image sensor 240 in the horizontal direction is α·N, the number of pixels of the image sensor 240 in the vertical direction is α·N, the number of pixels of the image output from the output section 350 in the horizontal direction is N, and the number of pixels of the image output from the output section 350 in the vertical direction is N, for convenience of explanation. The number (N×N) of pixels of the image output from the output section 350 is determined based on the number of pixels of the image displayed on the display section 400, for example. α is an arbitrary value that is larger than 1. Therefore, the image (α·N×α·N pixels) acquired by the image sensor 240 has a resolution higher than that of the image (output image) output from the output section 350.

Figure 3:
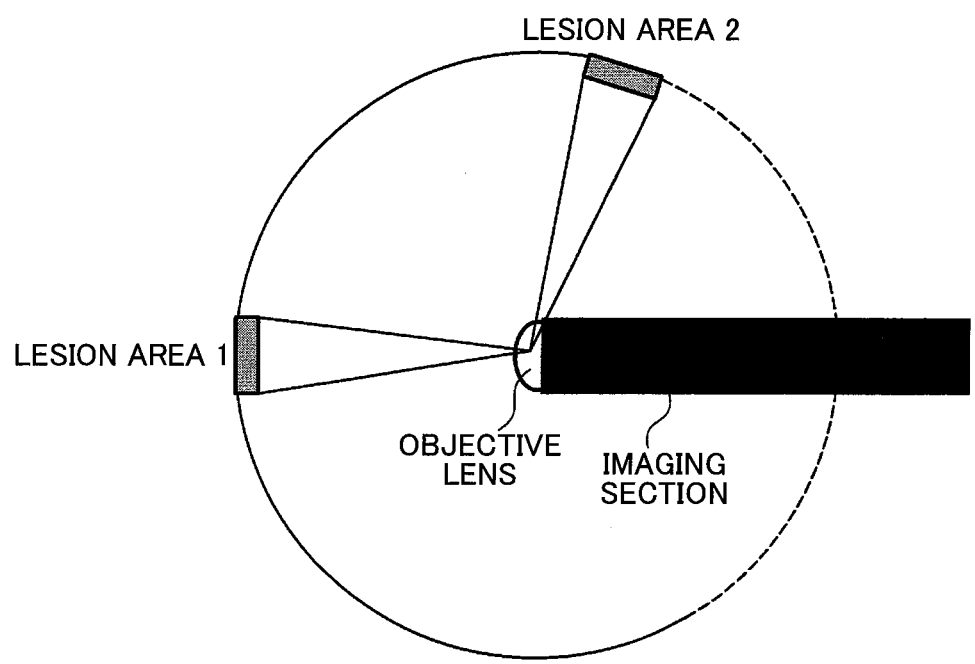
FIG. 3 illustrates an example in which a lesion area 1 and a lesion area 2 on a sphere are captured.
Figure 4:
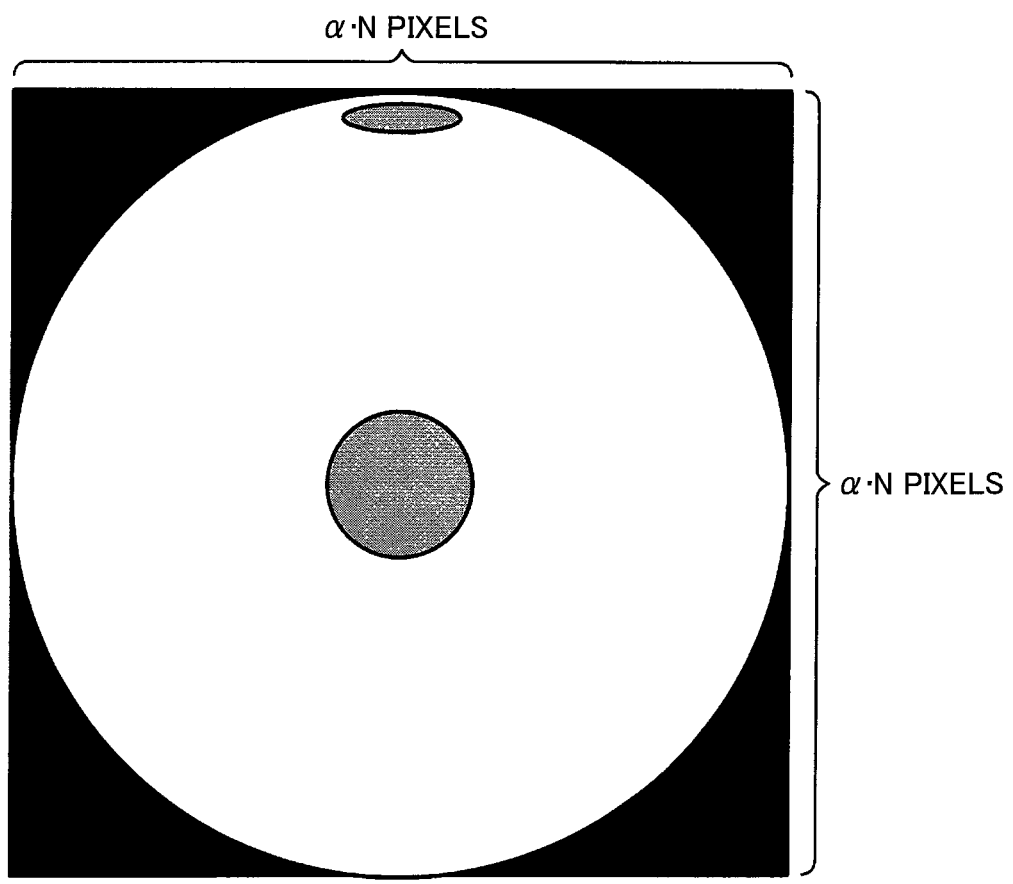
FIG. 4 illustrates an example of an original image that includes a lesion area 1 and a lesion area 2.

FIG. 3 is a view illustrating a state in which a lesion area 1 and a lesion area 2 situated on a spherical object are captured using the imaging section 200. FIG. 4 is a view illustrating an image output from the image processing section 320 to the scaling section 340 in such a state. The number of pixels of the image output from the image processing section 320 to the scaling section 340 is the same as the number (α·N×α·N) of pixels of the image sensor 240. Since the super-wide-angle optical system has a significantly large distortion, the local magnification in the peripheral area of the image is low as compared with the center area of the image. Therefore, the lesion area 2 situated in the peripheral area of the image is observed to have a size significantly smaller than that of the lesion area 1 situated in the center area of the image.

Figure 14:
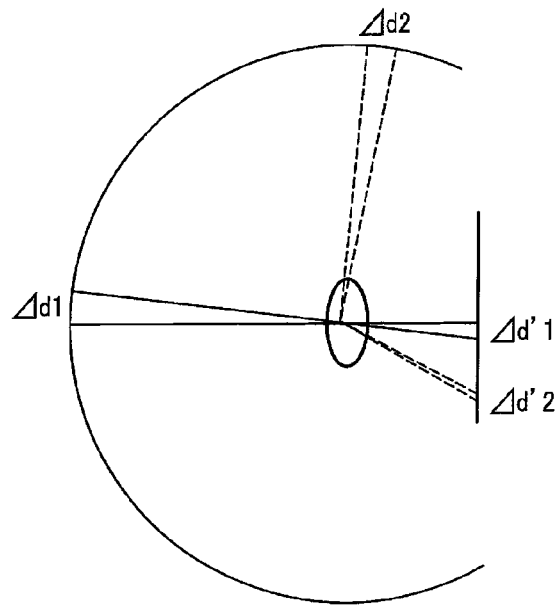
FIG. 14 is a view illustrating a local magnification according to one embodiment of the invention.

FIG. 14 is a view illustrating the concept of the local magnification. For example, the ratio of the distance Δd'1 or Δd'2 on the image sensor to the distance Δd1 or Δd2 on the spherical object when the entrance pupil of the objective lens is disposed near the center of the spherical object is determined to be the local magnification. Note that the distance Δd1 and the distance Δd2 are identical. Since the super-wide-angle optical system has a significantly large distortion, the local magnification Δd'2/Δd2 in the peripheral area of the image is lower than the local magnification Δd'1/Δd1 in the center area of the image.

The scaling section 340 acquires the coordinates (outX, outY) of the pixel of interest (pixel value calculation target pixel) of the image after the scaling process. The image after the scaling process is an N×N pixel image (see FIG. 6), and the coordinates (outX, outY) are coordinates based on the upper left pixel. The scaling section 340 converts the coordinates (outX, outY) of the pixel of interest into coordinates (shiftX, shiftY) based on the center of the image (i.e., the point of the image corresponding to the optical axis of the optical system) using the following expression (10) (see FIG. 7). Note that the coordinates (outCentX, outCentY) are coordinates of the center of the image after the scaling process.

$$\text{shift}X = \text{out}X - \text{out}\text{Cent}X$$

$$\text{shift}Y = \text{out}Y - \text{out}\text{Cent}Y \quad (10)$$

The scaling section 340 calculates the ratio ihOut using the following expression (11). Note that ihOut_max is the maximum distance from the center of the image within the image after the scaling process, and ihOut is the ratio of the distance from the center of the image to the pixel of interest to the maximum distance ihOut_max.

$$ihOut = \frac{\sqrt{\text{shift}X^2 + \text{shift}Y^2}}{ihOut\_Max} \quad (11)$$

The scaling section 340 calculates the value ihRatio using the ratio ihOut. The value ihRatio is determined by the ratio ihOut. For example, the data illustrated in FIG. 9 that indicates the relationship between the ratio ihOut and the value ihRatio is stored in a memory as a look-up table (LUT). The value ihRatio that corresponds to each ratio ihOut can be calculated by performing a linear interpolation process or the like using the LUT.

Figure 8:
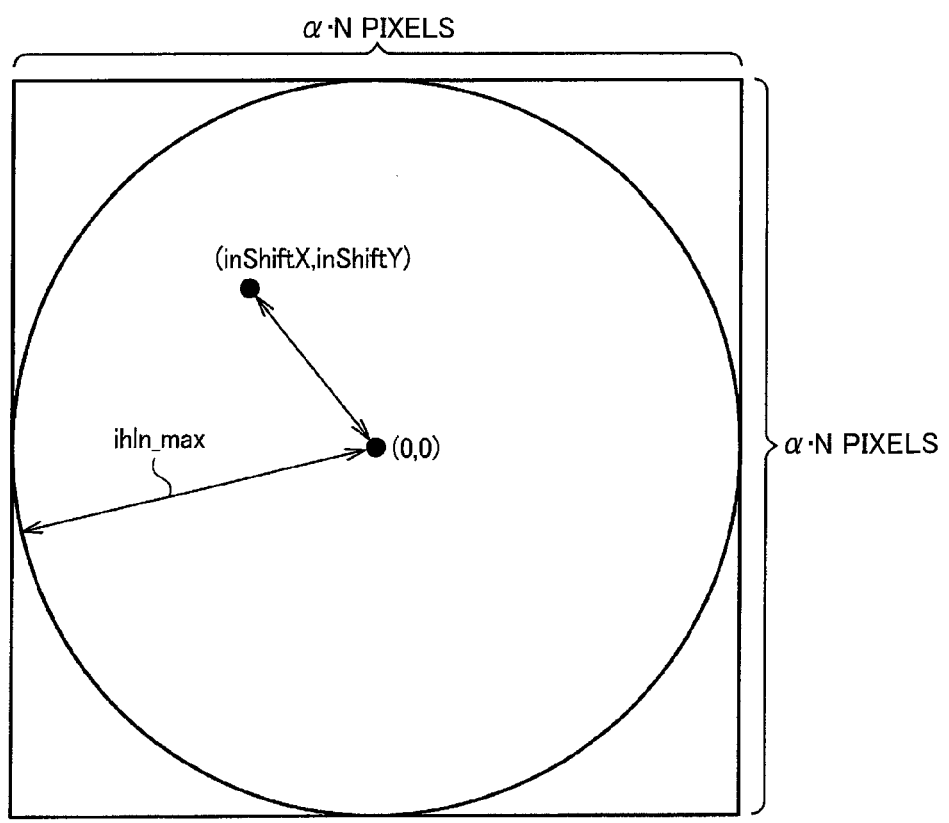
FIG. 8 illustrates an example of an original image in which the point that corresponds to the optical axis is set to be the origin.

The scaling section 340 calculates the coordinates (inShiftX, inShiftY) of the image before the scaling process that correspond to the coordinates (shiftX, shiftY) of the image after the scaling process from the calculated value ihRatio using the following expression (12). Note that the coordinates (inShiftX, inShiftY) are coordinates based on the center of the image before the scaling process (see FIG. 8).

$$\text{inShift}X = \text{shift}X * ihRatio * \alpha$$

$$\text{inShift}Y = \text{shift}Y * ihRatio * \alpha \quad (12)$$

The scaling section 340 converts the calculated coordinates (inShiftX, inShiftY) into the coordinates (inX, inY) based on the upper left pixel of the image using the following expression (13). Note that the coordinates (inCentX, inCentY) are the coordinates of the center of the image before the scaling process. The coordinates (inX, inY) are the coordinates of the image before the scaling process that correspond to the coordinates (outX, outY) of the pixel of interest of the image after the scaling process.

$$\text{in}X = \text{inShift}X + \text{inCent}X$$

$$\text{in}Y = \text{inShift}Y + \text{inCent}Y \quad (13)$$

Figure 11:
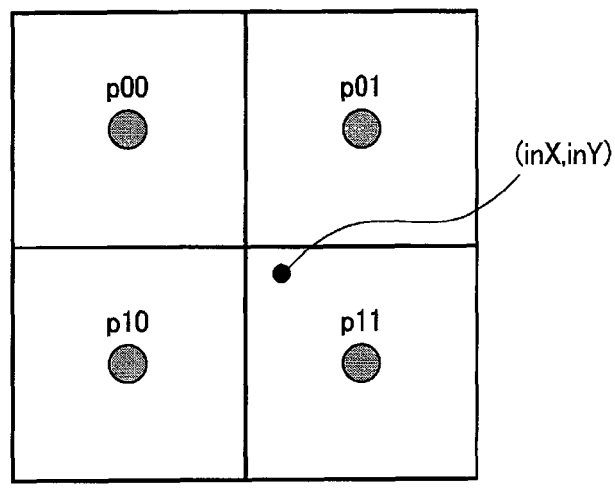
FIG. 11 is a view illustrating a bilinear method.

The scaling section 340 calculates the pixel value I(outX, outY) of the pixel of interest (outX, outY) of the image after the scaling process from the coordinates (inX, inY) of the image before the scaling process. For example, the pixel value of the pixel of interest is calculated using an interpolation process such as a nearest-neighbor interpolation process or a bilinear interpolation process. When using the nearest-neighbor interpolation process (see FIG. 11), the pixel value of a pixel p11 of the image before the scaling process that is nearest to the calculated coordinates (inX, inY) is determined to be the pixel value I(outX, outY) of the pixel of interest of the image after the scaling process. When using the bilinear interpolation process, the pixel value I(outX, outY) of the pixel of interest is calculated by the following expression (14) using the pixel values of the four pixels around the coordinates (inX, inY) of the image before the scaling process. Note that the pixel value I(outX, outY) of the pixel of interest may also be calculated by another known interpolation process.

$$I(outX, outY) = (\text{floor}(inX) + 1 - inX) * (\text{floor}(inY) + 1 - inY) * p00 + \quad (14)$$
$$(\text{floor}(inX) + 1 - inX) * (inY - \text{floor}(inY)) * p10 +$$
$$(inX - \text{floor}(inX)) * (\text{floor}(inY) + 1 - inY) * p01 +$$
$$(inX - \text{floor}(inX)) * (inY - \text{floor}(inY)) * p11$$

Figure 12:
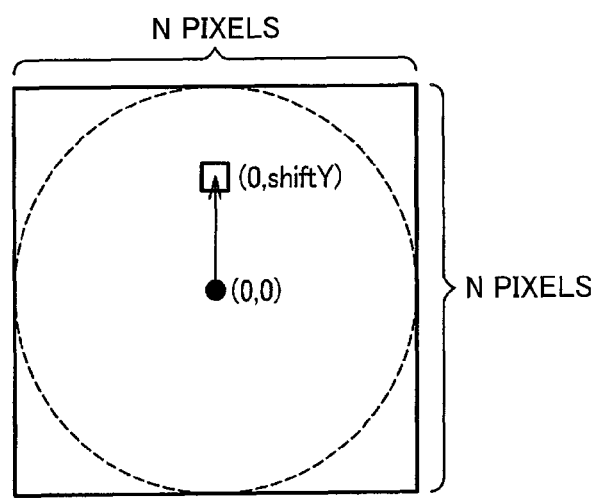
FIG. 12 illustrates an example of a scaled image for explaining a process when shiftX=0.
Figure 13:
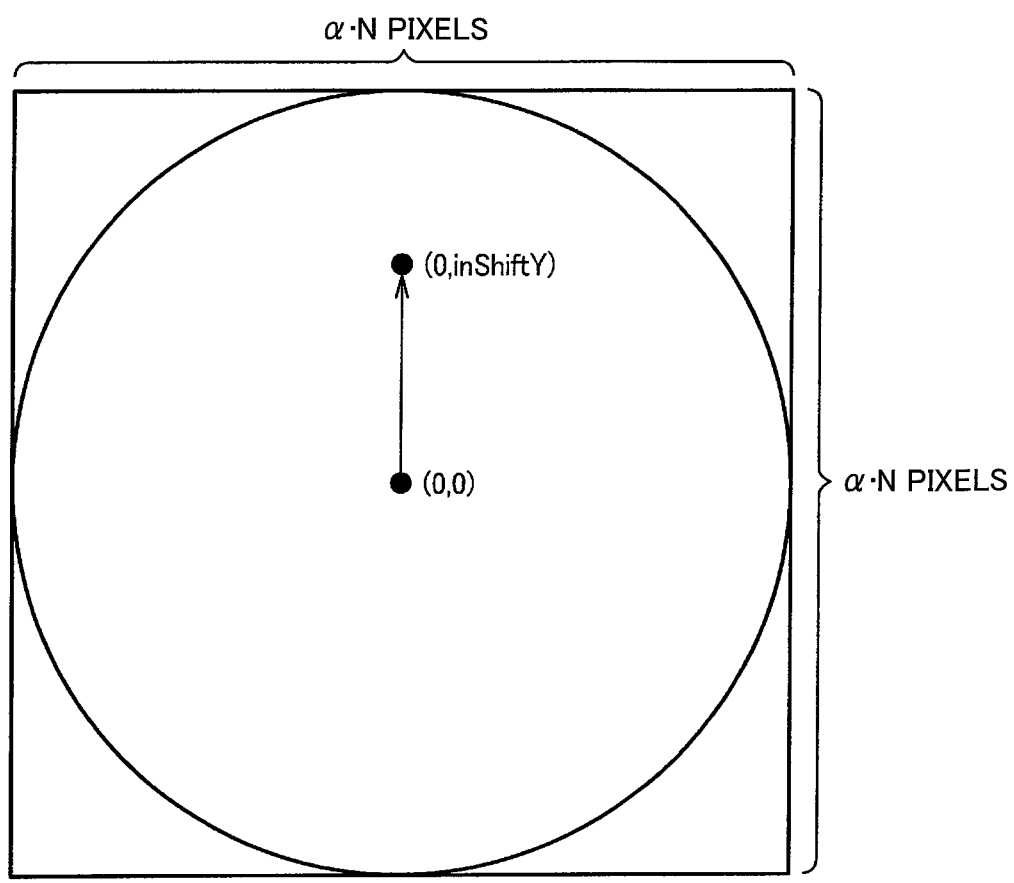
FIG. 13 illustrates an example of an original image for explaining a process when shiftX=0.

A method for calculating the data illustrated in FIG. 9 that indicates the relationship between the ratio ihOut and the value ihRatio is described below. The following description is given using the coordinate value shiftY when shiftX=0 and the corresponding coordinate value inShiftY for convenience of explanation. FIG. 10 illustrates the relationship between the coordinate value shiftY when shiftX=0 and the corresponding coordinate value inShiftY. The coordinate value inShiftX is 0 when the coordinate value shiftX is 0 (see the expression (12)). FIG. 10 illustrates the relationship between the coordinate value shiftY and the coordinate value inShiftY along the vertical straight line that passes through the center of the image (see FIGS. 12 and 13). Since the coordinate value shiftY is the coordinate value of the image after the scaling process based on the center of the image, the coordinate value shiftY is 0 to N/2. Since the coordinate value inShiftY is the coordinate value of the image before the scaling process based on the center of the image, the coordinate value inShiftY is 0 to ($\alpha \cdot N$)/2.

The embodiment of the invention aims at obtaining an output image in which the size of the lesion area 2 situated in the peripheral area of the image is relatively increased, and a deterioration in resolution due to the enlargement process occurs to only a small extent. In order to achieve the above object, the value ihRatio corresponding to the ratio ihOut is determined so that the scaling factor is 1 in the peripheral area of the image illustrated in FIG. 9, and the scaling factor is $\beta$ in the center area of the image illustrated in FIG. 9. Note that $\beta$ is an arbitrary positive value that is smaller than $1/\alpha$. The term "scaling factor" used herein refers to the ratio of the number of pixels of the image before the scaling process in the radial direction (i.e., the direction from the pixel of interest to the center of the image) to the number of pixels of the image after the scaling process in the radial direction. For example, the number of pixels of the image after the scaling process in the radial direction is equal to that of the image before the scaling process when the scaling factor is 1, and the number of pixels of the image after the scaling process in the radial direction is half of that of the image before the scaling process when the scaling factor is 0.5.

The value ihRatio is calculated for the peripheral area of the image so that the coordinate value inShiftY is ($\alpha \cdot N$)/2−i when the coordinate value shiftY is N/2−i. Note that i is an arbitrary positive number. Since the number of pixels of the image after the scaling process in the radial direction is equal to that of the image before the scaling process in the peripheral area of the image by thus calculating the value ihRatio, the resolution of the image after the scaling process is equal to that of the image before the scaling process. Specifically, the value ihRatio corresponding to an arbitrary value i is given by the following expression (15) by substituting ($\alpha \cdot N$)/2−i for inShiftY in the expression (12), substituting N/2−i for shiftY in the expression (12), and transforming the expression.

$$ihRatio = \frac{\alpha \cdot N - 2i}{\alpha(N - 2i)} \quad (15)$$

The value ihRatio is calculated for the center area of the image so that the coordinate value inShiftY is 1 when the coordinate value shiftY is $\beta \cdot 1$. Note that i is an arbitrary positive number. Since the number of pixels of the image after the scaling process in the radial direction is smaller than that of the image before the scaling process by a factor of $\beta$ (i.e., a reduction process by a factor of $\beta$ is performed) in the center area of the image by thus calculating the value ihRatio, the resolution of the image after the scaling process is lower than that of the image before the scaling process by a factor of $\beta$. Specifically, the value ihRatio corresponding to an arbitrary value i is given by the following expression (16) by substituting i for inShiftY in the expression (12), substituting $\beta \cdot i$ for shiftY in the expression (12), and transforming the expression.

$$ihRatio = \frac{1}{\alpha \cdot \beta} \quad (16)$$

The value ihRatio in the range between the center area and the peripheral area of the image may be set linearly so that the ratio ihRatio changes continuously (see FIG. 9) in order to prevent a situation in which the image after the scaling process becomes unnatural.

Figure 5:
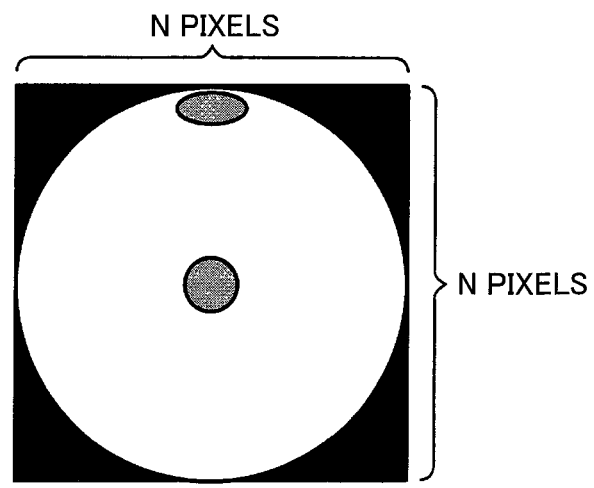
FIG. 5 illustrates an example of a scaled image obtained by performing a scaling process on an original image that includes a lesion area 1 and a lesion area 2.

Since the above process is performed axisymmetrically around the center of the image, the image after the scaling process has a configuration in which the image before the scaling process is reduced in the center area of the image, and the resolution before the scaling process is maintained in the peripheral area of the image (see FIG. 5). Therefore, an image in which the peripheral area of the image is relatively enlarged as compared with the center area of the image, and a deterioration in resolution due to the enlargement process is not observed, is displayed on the display section 400. This makes it possible for the user to observe a high-quality image in which the effects of distortion of the optical system are reduced, even when a lesion is situated in the peripheral area of the image.

Figure 9:
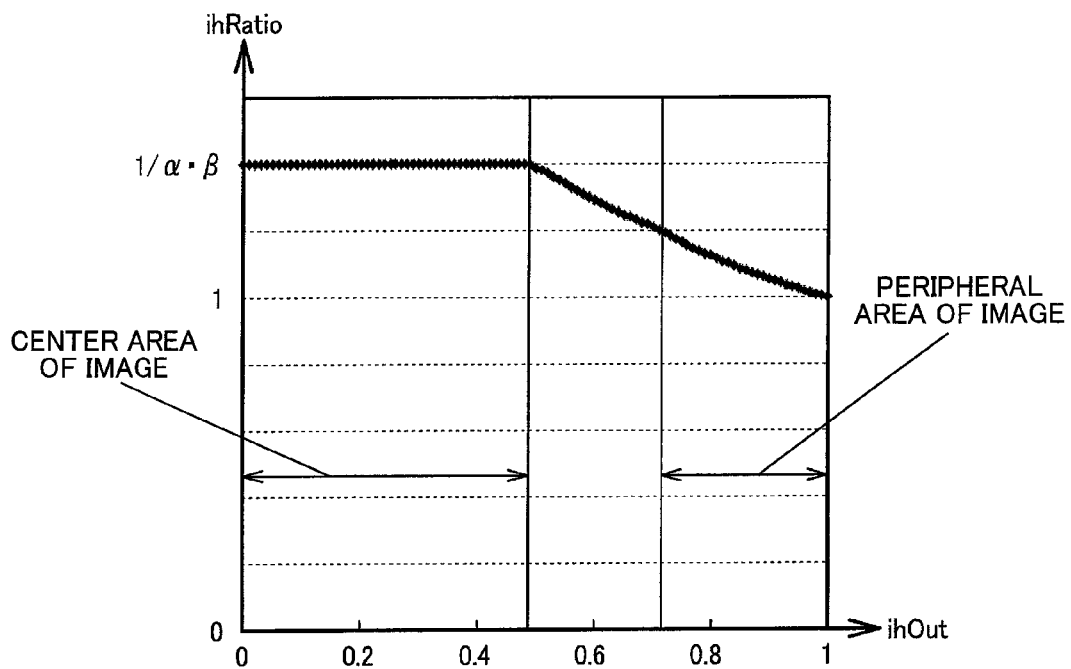
FIG. 9 is a view illustrating the relationship between a ratio ihOut and a value ihRatio.
Figure 10:
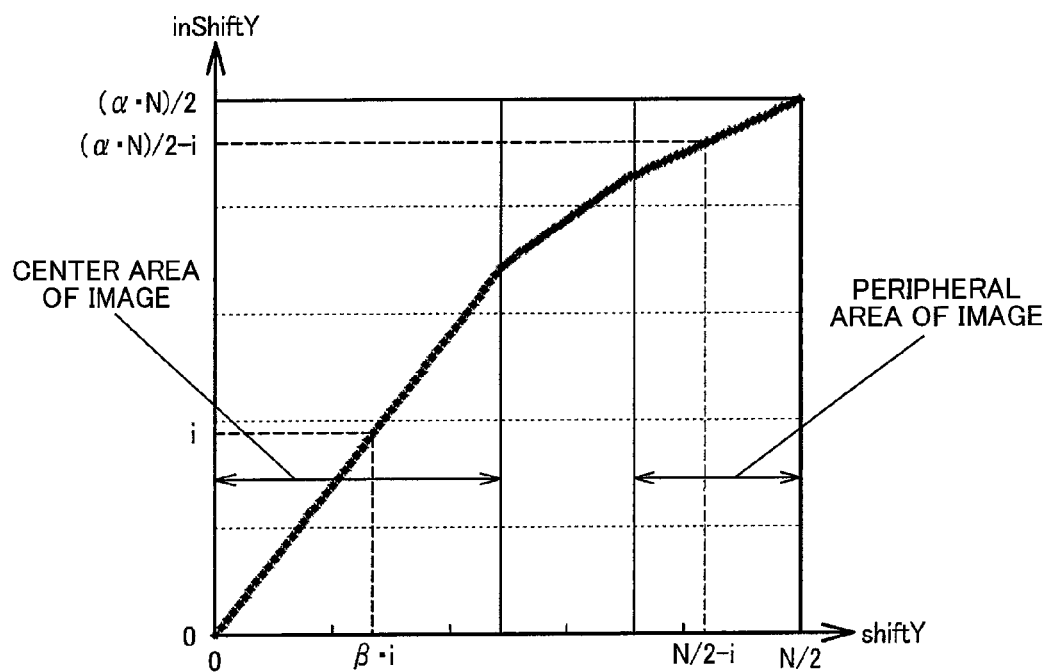
FIG. 10 is a view illustrating the relationship between coordinate values shiftY and inShiftY.

The magnification in the center area and the magnification in the peripheral area of the image after the scaling process can respectively be adjusted by adjusting the values of the LUT illustrated in FIG. 9 that indicates the relationship between the ratio ihOut and the value ihRatio. For example, the scaling process may be performed so that the image after the scaling process is enlarged as compared with the image before the scaling process (i.e., the scaling factor is set to be larger than 1) in the peripheral area of the image. In this case, the resolution in the peripheral area of the image is not improved as compared with the resolution of the image before the scaling process. However, a deterioration in image quality in the peripheral area of the image after the scaling process can be reduced by utilizing an image sensor having a number of pixels sufficiently larger than the number of pixels of the image output from the output section 350, as compared with the case of utilizing an image sensor having a number of pixels equal to or smaller than the number of pixels of the image output from the output section 350. Although an example in which the scaling factor changes steeply at the boundary between the center area and the peripheral area of the image has been described above, the value ihRatio may be adjusted so that the scaling factor changes gently.

A plurality of LUT that differ in the characteristic of the value ihRatio with respect to the ratio ihOut may be provided in advance, and the user may select the desired LUT by selecting a mode using the external I/F section 500. This makes it possible to implement a different scaling process that reflects the preference of the user.

Although an example in which the scaling factor in the peripheral area of the image is set to 1 has been described above, the configuration is not limited thereto. For example, the scaling factor in the peripheral area of the image may be set to γ (γ is an arbitrary value in the range of about 0.8 to about 1.2, for example). In this case, since the value ihRatio is 1 in the outermost area of the image (i.e., an area in which i=0) regardless of the value γ, the expression (12) can be used directly. The value ihRatio is calculated for the peripheral area of the image so that the coordinate value inShiftY is (α·N)/2−i when the coordinate value shiftY is N/2−γ·i. Note that i is an arbitrary positive number. The number of pixels of the image after the scaling process in the radial direction is larger or smaller than that of the image before the scaling process by a factor of γ in the peripheral area of the image by thus calculating the value ihRatio. Specifically, the value ihRatio corresponding to an arbitrary value i is given by the following expression (17) by substituting (α·N)/2−i for inShiftY in the expression (12), substituting N/2−γ·i for shiftY in the expression (12), and transforming the expression.

$$ihRatio = \frac{\alpha \cdot N - 2i}{\alpha(N - 2\gamma \cdot i)} \qquad (17)$$

Figure 15:
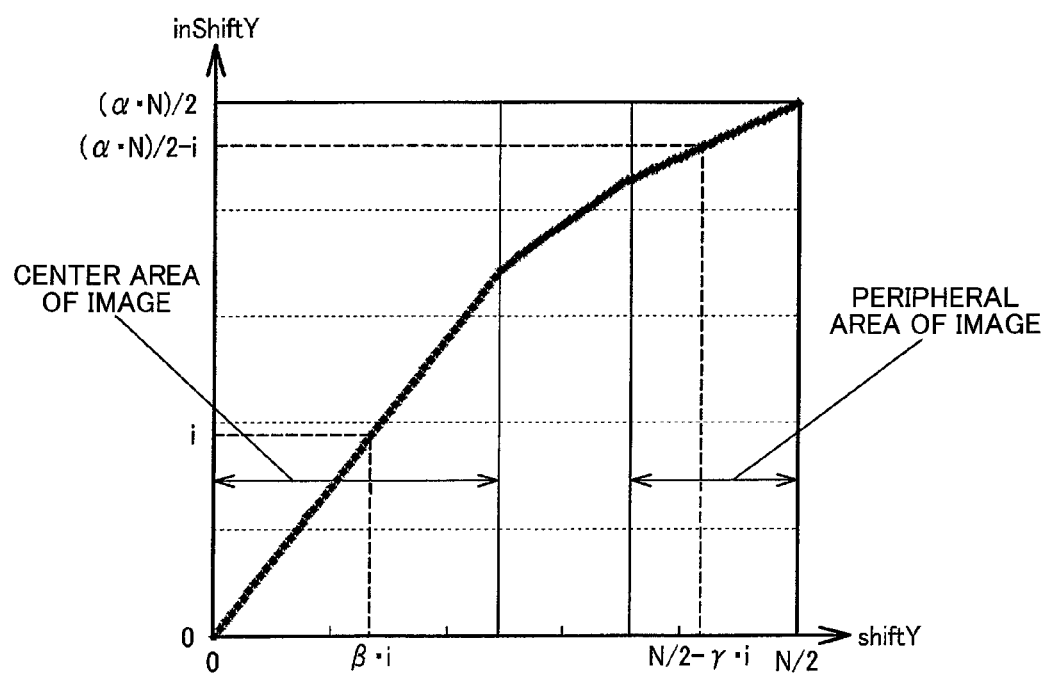
FIG. 15 is another view illustrating the relationship between coordinate values shiftY and inShiftY.

In this case, the coordinate values shiftY and inShiftY have the relationship illustrated in FIG. 15.

According to the above embodiments, the imaging device includes the image sensor 240 that includes a plurality of pixels that generate image signals from an object image that is formed by an imaging optical system, the scaling section 340 that performs the scaling process on an original image that is based on the image signals generated by the plurality of pixels, and the output section 350 that outputs an image obtained by the scaling process as a scaled image (see FIG. 1). The scaling section 340 performs a different scaling process corresponding to the position of the pixel of interest within the scaled image. The image sensor 240 includes pixels in a number larger than the number of pixels of the scaled image as the plurality of pixels.

This makes it possible to acquire the scaled image by capturing the original image (see FIG. 5) having a number of pixels larger than that of the scaled image to be output (FIG. 6), and performing the scaling process on the original image. It is possible to perform a process based on the position of the pixel of interest within the image by performing a different scaling process (e.g., a process that changes the scaling factor used for the scaling process) corresponding to the position of the pixel of interest. For example, the scaling factor is decreased in the center area of the image, and is increased in the peripheral area of the image (e.g., 1). Specifically, the scaled image in which distortion of the original image is canceled can be acquired by performing the process corresponding to the position of the pixel of interest, for example.

In this case, since it is unnecessary to perform an absolute enlargement process when relatively enlarging an area that is unclear due to distortion when the original image is larger than the scaled image, it is possible to suppress a deterioration in image quality in the target area. If the original image has a size equal to that of the scaled image, it is necessary to perform a process that enlarges a 50-pixel area to a 100-pixel area when enlarging the unclear area, for example. In this case, however, a deterioration in image quality occurs since the 50-pixel area includes only the information corresponding to the 50 pixels. In contrast, when a 100-pixel area of the original image (that is observed to be small and unclear within the large original image) is used directly, the 100-pixel area can be displayed directly within the scaled image (i.e., the 100-pixel area is relatively enlarged since the scaled image is small). Therefore, a deterioration in image quality does not occur.

When the ratio of the number of pixels of the corresponding side of the original image to the number of pixels of an arbitrary side of the scaled image is referred to as α, and β and γ are a value that satisfies β<(1/α)<γ, the scaling section 340 may set the scaling factor at the position of the pixel of interest that belongs to a first processing area within the scaled image to γ, and may set the scaling factor at the position of the pixel of interest that belongs to a second processing area that differs from the first processing area to β.

α indicates the ratio of the length of one side of the original image to the length of one side of the scaled image. For example, when the original image is a 200×200-pixel square image, and the scaled image is a 100×100-pixel square image, α is calculated to be 200/100=2.

This makes it possible to set the scaling factor to be larger than 1/α in the first processing area, and set the scaling factor to be smaller than 1/α in the second processing area. Since the ratio of the length of one side of the original image to the length of one side of the scaled image is α, the size of the original image can be adjusted to the size of the scaled image by performing the scaling process on the entire original image while setting the scaling factor to 1/α (i.e., a reduction process since α>1). However, distortion cannot be canceled when the scaling process is performed on the entire original image using an identical scaling factor. This problem can be solved by providing the second processing area that is subjected to the scaling process (strong reduction process) using a scaling factor smaller than 1/α, and the first processing area that is subjected to the scaling process (weak reduction process or enlargement process) using a scaling factor larger than 1/α. Therefore, since the first processing area is relatively enlarged as compared with the second processing area, distortion can be canceled.

When δ is a value that satisfies γ>δ>β, the scaling factor corresponding to a third processing area that differs from the first processing area and the second processing area may be set to δ.

This makes it possible to flexibly set the scaling factor corresponding to the position of the area without limiting the scaling factor to two values. It is thus possible to prevent a rapid change in the image at the boundary between the areas, and provide an image that can be easily observed by the user, for example.

The scaling section 340 may use a value that is set within a given value range that includes 1 as the scaling factor γ at the position of the pixel of interest that belongs to the first processing area. For example, a value that is set within the range of 0.5 to 2.0 may be used as the scaling factor γ. It is desirable to use a value that is set within the range of 0.8 to 1.2 as the scaling factor γ.

This makes it possible to use 1 or a value close to 1 as the scaling factor γ. When the scaling factor γ is set to 1 (i.e., the scaling factor is set to 1 at the position of the pixel of interest that belongs to the first processing area), the number of pixels of the original image in the radial direction is equal to that of the scaled image in the first processing area. This makes it possible to suppress a situation in which the image quality deteriorates, or the information is lost. Note that the scaling factor γ is not limited to 1, but may be changed to such an extent that the image quality of the scaled image does not significantly deteriorate. For example, the image may be reduced to some extent (the information may be lost in this case since some pixels are lost), or may be enlarged to some extent (the image quality may deteriorate in this case).

The scaling section 340 may set the scaling factor at the position of the pixel of interest based on the distance between the pixel of interest and a point within the scaled image that corresponds to the optical axis of the imaging optical system.

Note that the point within the scaled image that corresponds to the optical axis of the imaging optical system normally corresponds to the center point of the scaled image. For example, the point within the scaled image that corresponds to the optical axis of the imaging optical system corresponds to the point (outCentX, outCentY) in FIG. 6 or the point (0, 0) in FIG. 7. Note that the point within the scaled image that corresponds to the optical axis of the imaging optical system is not limited thereto.

This makes it possible to flexibly set the scaling factor corresponding to the distance between the point that corresponds to the optical axis and the pixel of interest. When using an optical system having a wide angle of view (e.g., fish-eye lens), an area positioned away from the point that corresponds to the optical axis is unclear due to distortion or the like as compared with an area positioned close to the point that corresponds to the optical axis. For example, a lesion area having an identical size is appropriately displayed in the center area, but becomes small and unclear in the peripheral area (see FIG. 4). Specifically, it is possible to set the scaling factor corresponding to the optical system by setting the scaling factor corresponding to the distance from the point that corresponds to the optical axis.

The scaling section 340 may set an area that is positioned at a long distance from the point that corresponds to the optical axis of the imaging optical system to be an image peripheral area, and may set an area that is positioned at a short distance from the point that corresponds to the optical axis of the imaging optical system as compared with the image peripheral area to be an image center area. The scaling section 340 may set a different scaling factor in the image peripheral area and the image center area.

Figure 6:
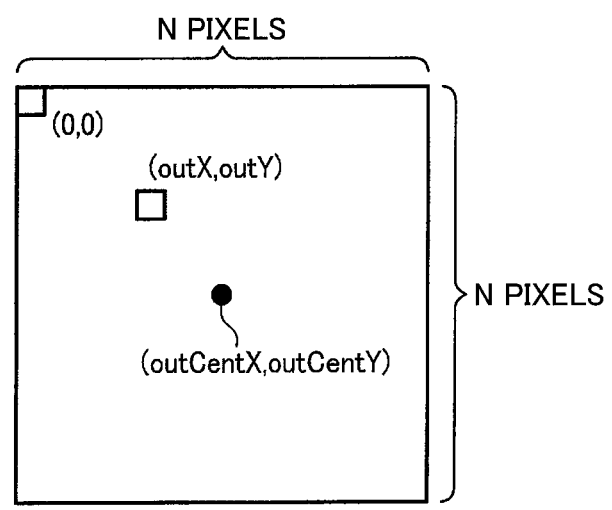
FIG. 6 illustrates an example of a scaled image in which the upper left point of the image is set to be the origin.
Figure 7:
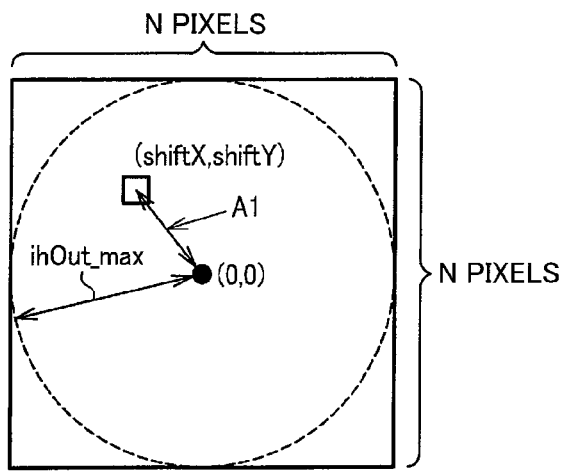
FIG. 7 illustrates an example of a scaled image in which the point that corresponds to the optical axis is set to be the origin.

This makes it possible to define the image peripheral area and the image center area using the distance from the point that corresponds to the optical axis. In FIGS. 6 and 7, whether the area is the image center area or the image peripheral area is determined based on the point (outCentX, outCentY) or (0, 0) that corresponds to the optical axis, and is irrelevant to the apparent center point (N/2, N/2). This is because distortion of the image is determined based on the point (outCentX, outCentY) or (0, 0), and is irrelevant to the point (N/2, N/2).

When α and γ are a value that satisfies $(1/\alpha)<\gamma$, the scaling section 340 may set the scaling factor in the image peripheral area to γ by performing a process that determines the pixel value of the pixel of interest that belongs to the image peripheral area within the scaled image based on the pixel values of the pixels among the pixels that belong to an area within the original image that corresponds to the image peripheral area that are extracted every 1/γ pixels.

Since γ is a value that satisfies $(1/\alpha)<\gamma$, γ may be larger than 1. In this case, 1/γ is equal to or smaller than 1. Therefore, the process that extracts the pixels every 1/γ pixels is defined as described below. Specifically, when $(1/\gamma)>1$, a thinning process is performed directly. When $(1/\gamma)<1$, an enlargement process that enlarges one pixel to γ pixels is performed. For example, when γ=2, the pixels are extracted every 0.5 pixels. Therefore, an enlargement process that enlarges one pixel to two pixels is performed. Note that the above process may be performed using the nearest-neighbor method or the like.

Figure 18:
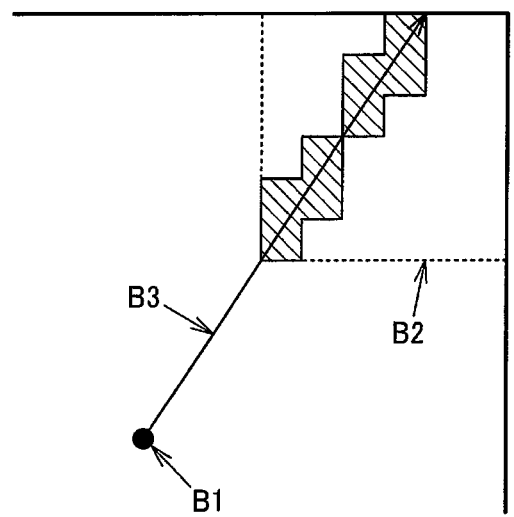
FIG. 18 is a view illustrating the target pixels when performing a pixel thinning process.

The above configuration makes it possible to implement the scaling process by performing a pixel thinning process (or an enlargement process). Note that 1/γ pixels when extracting the pixels every 1/γ pixels are calculated in the vector direction that connects the point within the original image that corresponds to the optical axis and the point within the original image that corresponds to the pixel of interest. For example, when the point within the original image that corresponds to the optical axis and the point within the original image that corresponds to the pixel of interest are positioned on an identical vertical axis (see FIGS. 12 and 13), the pixels are extracted every 1/γ pixels in the direction along the vertical axis. As illustrated in FIG. 18, when the point that corresponds to the optical axis is referred to as B1, the image peripheral area is referred to as B2, and the vector that connects the point that corresponds to the optical axis and the point that corresponds to the pixel of interest is referred to as B3, the pixels are diagonally extracted every 1/γ pixels from the hatched pixels. The above process may be performed using the nearest-neighbor method or the like. Note that the pixels are extracted every pixels when γ=1. In this case, the original image and the scaled image are identical as to the size of the image peripheral area in the radial direction.

When α and β are a value that satisfies $\beta<(1/\alpha)$, the scaling section 340 may set the scaling factor in the image peripheral area to β by performing a process that determines the pixel value of the pixel of interest that belongs to the image peripheral area within the scaled image based on the pixel values of the pixels among the pixels that belong to an area within the original image that corresponds to the image peripheral area that are extracted every 1/β pixels.

Since $\beta<(1/\alpha)<1$, it is unnecessary to take account of the above enlargement process.

The above configuration makes it possible to implement the scaling process by performing a pixel thinning process. A specific method is the same as that employed when using γ. Therefore, detailed description thereof is omitted.

The image sensor 240 may acquire image signals that differ in local magnification corresponding to the position within the original image due to the effects of distortion of the imaging optical system, as image signals that correspond to the original image. The scaling section 340 may set the scaling factor based on the local magnification of the attention point within the original image that corresponds to the pixel of interest within the scaled image.

The local magnification is defined by the ratio of the distance Δd'1 to the distance Δd1, or the ratio of the distance Δd'2 to the distance Δd2 (see FIG. 14). In the example illustrated in FIG. 14, the local magnification defined by the ratio of the distance Δd'2 to the distance Δd2 (see the dotted lines) is lower than the local magnification defined by the ratio of the distance Δd'1 to the distance Δd1 (see the solid lines).

The above configuration makes it possible to implement the scaling process based on the local magnification. Since whether the target area is displayed as a large area or a small and unclear area is determined based on the local magnification, it is possible to perform an appropriate distortion correction process on the unclear area by performing a process based on the local magnification.

The scaling section 340 may set the scaling factor in an area in which the local magnification is low as compared with another area to be larger than the scaling factor in the other area.

This makes it possible to set a large scaling factor in an area in which the local magnification is relatively low (i.e., a small and unclear area) as compared with an area in which the local magnification is relatively high (i.e., a relatively clear area). It is thus possible to perform an appropriate distortion correction process on the unclear area.

When the local magnification at the attention point within the original image that corresponds to the image peripheral area is lower than the local magnification at the attention point within the original image that corresponds to the image center area, the scaling section 340 may set the scaling factor in the image peripheral area to be larger than the scaling factor in the image center area.

This makes it possible to relatively enlarge the image peripheral area as compared with the image center area, and cancel distortion. According to the above configuration, the image peripheral area and the image center area are defined using the local magnification.

The imaging device may further include the display section 400. The scaling section 340 may set the scaling factor at the position of the pixel of interest that belongs to the first processing area to $\gamma$ even when the entire scaled image is displayed on the display section.

This makes it possible to set the scaling factor in a specific area (first processing area) to $\gamma$ while displaying the entire image. $\gamma$ is a value of about 1. A system has been known in which the number of pixels of the display section is smaller than the number of pixels of the image acquired by the imaging optical system (e.g., the rear liquid crystal panel of a digital still camera). However, such a system is designed so that the entire image is reduced to large extent (i.e., the scaling factor is considerably small), and a scaling factor of about 1 is not set. In order to display an image while setting the scaling factor to about 1 (i.e., a resolution almost equal to that of the image acquired using the imaging optical system), it is necessary to display only a specific area on the display section in an enlarged state. According to the above method, however, it is possible to adjust the scaling factor in each area so that the entire image is displayed instead of displaying only a specific area while setting the scaling factor in the specific area to be about 1.

The image sensor 240 may acquire image signals that undergo distortion due to the effects of distortion of the imaging optical system as image signals that correspond to the original image.

This makes it possible to acquire an image that is distorted due to the effects of distortion using the image sensor 240. Various types of distortion (e.g., barrel distortion) have been known, and it is possible to efficiently perform a distortion correction process by taking the optical characteristics of distortion into consideration.

The imaging optical system may have an angle of view equal to or greater than 180°.

This makes it possible to utilize an imaging optical system having a wide angle of view. For example, when the imaging device is used for endoscope applications, it is possible to effectively find a lesion area situated on the back side of the folds of a large intestine or the like.

When an area that includes the optical axis of the imaging optical system is referred to as a front area, and an area that includes an axis that is orthogonal to the optical axis is referred to as a side area, the imaging optical system may be an optical system that can image an imaging area that is set within the front area or the side area.

Figure 17:
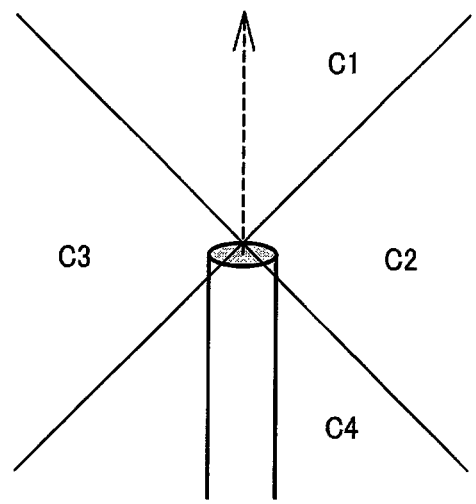
FIG. 17 is a view illustrating a front area, a side area, and a rear area with respect to the optical axis of an imaging optical system.

The front area and the side area are defined as illustrated in FIG. 17. C1 in FIG. 17 indicates the front area, and C2 and C3 in FIG. 17 indicate the side area. Although each area is two-dimensionally illustrated in FIG. 17, each area may be a three-dimensional area.

The above configuration makes it possible to set the imaging area within the front area or the side area, and image a wide area.

When an area that includes an axis that is in the direction opposite to the optical axis direction of the imaging optical system is referred to as a rear area, the imaging optical system may be an optical system that can image an imaging area that is set within the rear area.

The rear area is defined as illustrated in FIG. 17 (see C4). The rear area may be a three-dimensional area.

The above configuration makes it possible to also set the imaging area within the rear area. As a result, since a wide area can be imaged, it is possible to efficiently search a lesion area in endoscope applications or the like.

The scaling section 340 may change the scaling process based on a scaling mode change instruction issued by the user.

This makes it possible to implement the scaling process that reflects the operation instruction issued by the user, and more flexibly perform the scaling process. For example, even if the image quality has deteriorated due to the scaling process, the scaling process is appropriate when the deterioration cannot be visually observed by the user. Therefore, the scaled image after the scaling process set by the user may be presented to the user, and the user may set the allowable range based on the visual observation result.

The imaging device may be an endoscope apparatus.

This makes it possible to utilize the imaging device as an endoscope apparatus. Since the endoscope apparatus is used to search a lesion area, for example, the capability to observe a wide range is advantageous. Since a part that blocks the view (e.g., the folds of a large intestine) is present inside a living body, it is desirable that such a part can be observed with a wide angle of view so that it is unnecessary to insert the imaging section into the back side of each fold. It is possible to meet such a demand by utilizing the imaging device as an endoscope apparatus.

The above embodiments also relate to an imaging method that includes acquiring an original image based on image signals at a plurality of pixels that generate an image signal from an object image that is formed by an imaging optical system, performing the scaling process on the original image using a different scaling factor corresponding to the position of the pixel of interest to acquire a scaled image that is an image having a number of pixels smaller than that of the original image, and outputting an image after the scaling process as the scaled image.

This makes it possible to implement an imaging method that utilizes the method according to the above embodiments.

Although only some embodiments of the present invention have been described in detail above, those skilled in the art will readily appreciate that many modifications are possible in the embodiments without materially departing from the novel teachings and advantages of this invention. Accordingly, such modifications are intended to be included within the scope of the invention. Any term cited with a different term having a broader meaning or the same meaning at least once in the specification and the drawings can be replaced by the different term in any place in the specification and the drawings. The configuration and the operation of the imaging device and the like are not limited to those described in connection with the above embodiments. Various modifications and variations may be made.

What is claimed is:

1. An endoscope apparatus comprising:
an image sensor that includes a plurality of pixels that generate image signals from an object image that is formed by an imaging optical system;
a scaling section that generates a scaled image that is an image having a number of pixels smaller than a number of pixels of an original image by performing a scaling process on the original image, the original image being based on the image signals generated by the plurality of pixels; and
an output section that outputs the scaled image, wherein:
the scaling section performs the scaling process using a different scaling factor corresponding to a position of a pixel of interest within the scaled image, the scaling factor being a ratio of a number of pixels of the image before the scaling process in a processing area in a direction toward the center of the image to the number of pixels of the image after the scaling process in the processing area in the direction toward the center of the image, and the processing area being an area that includes the pixel of interest,
the scaling section sets the scaling factor at the position of the pixel of interest that belongs to a first processing area within the scaled image to γ, and sets the scaling factor at the position of the pixel of interest that belongs to a second processing area within the scaled image that differs from the first processing area to β, with β and γ being values that satisfy $\beta<(1/\alpha)<\gamma$, and α being a ratio of a number of pixels of a corresponding side of the original image to a number of pixels of an arbitrary side of the scaled image,
the second processing area is an area that includes a point corresponding to an optical axis of the imaging optical system on the scaled image, and
the scaling section uses a value that is set within a given value range that includes 1 as the scaling factor γ at the position of the pixel of interest that belongs to the first processing area.

2. The endoscope apparatus as defined in claim 1, wherein the scaling section sets the scaling factor corresponding to a third processing area that differs from the first processing area and the second processing area to δ, with δ being a value that satisfies $\gamma>\delta>\beta$.

3. The endoscope apparatus as defined in claim 1, wherein the scaling section uses a value that is set within a range of 0.5 to 2.0 as the scaling factor γ at the position of the pixel of interest that belongs to the first processing area.

4. The endoscope apparatus as defined in claim 3, wherein the scaling section uses a value that is set within a range of 0.8 to 1.2 as the scaling factor γ at the position of the pixel of interest that belongs to the first processing area.

5. The endoscope apparatus as defined in claim 1, wherein the scaling section sets the scaling factor at the position of the pixel of interest based on a distance between the pixel of interest and the point corresponding to the optical axis of the imaging optical system.

6. The endoscope apparatus as defined in claim 5, wherein the scaling section sets an area in which the distance between the pixel of interest and the point corresponding to the optical axis of the imaging optical system is long to be an image peripheral area, sets an area in which the distance between the pixel of interest and the point corresponding to the optical axis of the imaging optical system is short as compared with the image peripheral area to be an image center area, and sets a different scaling factor in the image peripheral area and the image center area.

7. The endoscope apparatus as defined in claim 6, wherein the scaling section sets the scaling factor in the image peripheral area to γ by performing a process that determines a pixel value of a pixel of interest that belongs to the image peripheral area within the scaled image based on pixel values of pixels, from among pixels that belong to an area within the original image that corresponds to the image peripheral area, that are extracted every 1/γ pixels, with γ being a value that satisfies $(1/\alpha)<\gamma$, and α being a ratio of a number of pixels of a corresponding side of the original image to a number of pixels of an arbitrary side of the scaled image.

8. The endoscope apparatus as defined in claim 6, wherein the scaling section sets the scaling factor in the image center area to β by performing a process that determines a pixel value of a pixel of interest that belongs to the image center area within the scaled image based on pixel values of pixels, from among pixels that belong to an area within the original image that corresponds to the image center area, that are extracted every 1/β pixels, with β being a value that satisfies $\beta<(1/\alpha)$, and α being a ratio of a number of pixels of a corresponding side of the original image to a number of pixels of an arbitrary side of the scaled image.

9. The endoscope apparatus as defined in claim 1, wherein:
the image sensor acquires image signals that differ in local magnification corresponding to a position within the original image due to effects of distortion of the imaging optical system, as image signals that correspond to the original image, the local magnification being a local magnification of the imaging optical system, and
the scaling section sets the scaling factor of the pixel of interest based on the local magnification of an attention point within the original image that corresponds to the pixel of interest within the scaled image.

10. The endoscope apparatus as defined in claim 9, wherein:
the scaling section sets the scaling factor used for the scaling process to be larger than the scaling factor in another area within the original image when the local magnification of the attention point within the original image that corresponds to the pixel of interest within the scaled image is lower than the local magnification in another area within the original image.

11. The endoscope apparatus as defined in claim 10, wherein:
the scaling section sets the scaling factor of the pixel of interest positioned in a peripheral area of the scaled image to be larger than the scaling factor of the pixel of interest positioned in a center area of the scaled image when the local magnification of the attention point within the original image that corresponds to the pixel of interest positioned in the peripheral area of the scaled image is lower than the local magnification of the attention point within the original image that corresponds to the pixel of interest positioned in a center area of the scaled image.

12. The endoscope apparatus as defined in claim 1, further comprising:

a display section that displays the scaled image,
wherein the scaling section sets the scaling factor at the position of the pixel of interest that belongs to the first processing area to γ even when an entirety of the scaled image is displayed on the display section.

13. The endoscope apparatus as defined in claim 1, wherein the image sensor acquires image signals that undergo distortion due to effects of distortion of the imaging optical system as image signals that correspond to the original image.

14. The endoscope apparatus as defined in claim 1, wherein the imaging optical system has an angle of view equal to or greater than 180°.

15. The endoscope apparatus as defined in claim 1, wherein the imaging optical system comprises an optical system that can image an imaging area that is set within a front area or a side area, the front area being an area that includes the optical axis of the imaging optical system, and the side area being an area that includes an axis that is orthogonal to the optical axis.

16. The endoscope apparatus as defined in claim 15, wherein the imaging optical system comprises an optical system that can image an imaging area that is set within a rear area, the rear area being an area that includes an axis that is in a direction opposite to an optical axis direction of the imaging optical system.

17. The endoscope apparatus as defined in claim 1, wherein the scaling section changes the scaling process based on a scaling mode change instruction issued by a user.

18. An imaging method of an endoscope apparatus, the method comprising:

acquiring an original image based on image signals generated by a plurality of pixels that generate image signals from an object image that is formed by an imaging optical system;

generating a scaled image that is an image having a number of pixels smaller than a number of pixels of the original image by performing a scaling process on the original image, the scaling process using a different scaling factor corresponding to a position of a pixel of interest within the scaled image, the scaling factor being a ratio of a number of pixels of the image before the scaling process in a processing area in a direction toward the center of the image to the number of pixels of the image after the scaling process in the processing area in the direction toward the center of the image, and the processing area being an area that includes the pixel of interest; and outputting the scaled image, wherein:

performing the scaling process comprises setting the scaling factor at the position of the pixel of interest that belongs to a first processing area within the scaled image to γ, and setting the scaling factor at the position of the pixel of interest that belongs to a second processing area within the scaled image that differs from the first processing area to β, with β and γ being values that satisfy β<(1/α)<γ, and α being a ratio of a number of pixels of a corresponding side of the original image to a number of pixels of an arbitrary side of the scaled image, the second processing area is an area that includes a point corresponding to an optical axis of the imaging optical system on the scaled image, and wherein the scaling process uses a value that is set within a given value range that includes 1 as the scaling factor γ at the position of the pixel of interest that belongs to the first processing area.

\* \* \* \* \*